United States Patent [19]

Hayashibe et al.

[11] Patent Number: 5,624,846

[45] Date of Patent: Apr. 29, 1997

[54] CONTINUOUS FLOW ANALYZING METHOD AND APPARATUS

[75] Inventors: Yutaka Hayashibe; Yasumasa Sayama, both of Omiya, Japan

[73] Assignee: Mitsubishi Materials Corporation, Tokyo, Japan

[21] Appl. No.: 430,735

[22] Filed: Apr. 28, 1995

[30] Foreign Application Priority Data

Apr. 28, 1994 [JP] Japan .................................. 6-113468
Jun. 10, 1994 [JP] Japan .................................. 6-129263

[51] Int. Cl.[6] .................................................. G01N 35/08
[52] U.S. Cl. .................... 436/50; 436/52; 436/55; 436/73; 436/81; 436/166; 436/175; 436/177; 436/178; 422/62; 422/81; 422/82; 422/108
[58] Field of Search ............................... 422/62, 81, 82, 422/108; 436/52, 55, 73, 81, 166, 172, 175, 177, 178, 50

[56] References Cited

U.S. PATENT DOCUMENTS

| H1310 | 5/1994 | Peterson et al. ........................... 436/74 |
| 4,080,171 | 3/1978 | Sano et al. .................................. 23/253 |
| 5,178,771 | 1/1993 | Hayashibe et al. ...................... 210/709 |
| 5,387,524 | 2/1995 | Hayashibe et al. ........................ 436/74 |

OTHER PUBLICATIONS

F. Malamas et al. *Anal. Chim. Acta* 1984, 160, 1–10.
J. L. Burguera et al. *Anal. Chim. Acta* 1989, 234, 253–257.
M. Sollacaro et al. *J. Auto. Chem.* 1992, 14, 101–105.
B. Welz et al. *Anal. Chim. Acta* 1992, 261, 477–487.
D.J. Hooley et al. *Anal. Chem.* 1983, 55, 313–320.
D. Betteridge et al. *Anal. Chem*, 1986, 58, 2258–2265.
K. W. Simonsen et al. *J. Anal. Atom. Spectrom.* 1986, 1, 453–456.
B. Xia et al. *Youkuangye* 1993, 12, 38–45.
O. Navratil et al. *Anal Chim. Acta.* 1970, 52, 221–227.
S. Shibata et al. *Anal. Chim Acta* 1976, 82, 169–174.
E. M. Sitnikova *Chem. Abstr.* 1976, 85, 201620f.
K. Yoshimura et al. *Mem. Fac. Sci. Kyushu Univ., Ser. C* 1979, 11, 181–188.
J. Ruzicka et al. *Anal. Chim. Acta* 1980, 114, 19–44.
J.L. Burguera et al. *Anal. Chim Acta* 1981, 127, 199–201.
L. Gorton et al. *Anal. Chim. Acta* 1981, 130, 45–53.
D.J. Hooley et al. *Chem. Abstr.* 1983, 98, 45998w.
D. Betteridge et al. *Chem. Abstr.* 1983, 99, 10931n.
S. S. Jorgensen et al. *Anal. Chim. Acta* 1985, 169, 51–57.
A. F. Kapauan et al. *Anal. Chem.* 1986, 58, 509–510.
K. W. Simonsen et al. *Chem. Abstr.* 1987, 106, 46716y.
A. M. Band et al. *Anal. Chim. Acta* 1987, 200, 213–225.

(List continued on next page.)

*Primary Examiner*—Arlen Soderquist
*Attorney, Agent, or Firm*—Ronald J. Kubovcik

[57] ABSTRACT

A continuous flow analyzing method and an apparatus for carrying out the analyzing method wherein a sample is injected in a continuously flowing carrier and the sample is introduced into a detector by the carrier to thereby perform a quantitative analysis contained in the sample. In the method the sample to be analyzed is filled into a sample introduction switchover valve (SISV); a portion of the sample from the SISV is injected into the carrier and an analysis of this sample is conducted to obtain a detection peak for the analyzed sample. These steps are repeated and the sample is continuously analyzed by, in the case where a detection peak obtained in the detector is under an optimum analysis range, increasing an injection amount of the sample, and in the case where the detection peak obtained in the detector is over the optimum range, decreasing the injection amount of the sample. Adjustment of the detection peak is repeated until the detection peak reaches the optimum analysis range. Since it is possible to precisely control the injection amount of the sample, it is possible to conduct a high precision quantitative analysis. It is possible to apply the method to a sample having a concentration as low as about 1 ng/ml up to a concentration as high as about 1,000 μg/m with the same apparatus system by feeding the results obtained in a detector back to a sample feed system.

9 Claims, 7 Drawing Sheets

OTHER PUBLICATIONS

J. Ruz et al. *Chem. Abstr.* 1988, 108, 50755u.

C. Thommen et al. *Ersenius Z. Anal. Chem.* 1988, 329, 678–684.

H. K. Chung et al. *Anal. Chem.* 1990, 62, 2541–2547.

M. I. Nasir et al. *Indian J. Chem.* 1992, 31A, 285–287.

A. Katti et al. *J. Chromatog.* 1992, 590, 127–132.

T. Becker et al. *J. Biotech.* 1993, 31, 267–275.

B. Freire dos Reis et al. *Analyst* 1993, 118, 719–722.

B. Xia et al. *Chem. Abstr.* 1994 120, 234898x.

M. Jarosz, *Chem. Anal.*, 1986, 31, 713–717.

E. R. Baggott, et al., *Analyst*, 1955, 80, 53–64.

S. Raptis, et al., *Clin. Chim. Acta*, 1978, 88, 393–402.

H. Chung–Gin, et al., *Talanta*, 1980, 27, 676–678.

H. Watanabe, et al., *Talanta*, 1979, 26, 959–961.

T. C. Chou et al., *Chem. Abstr.*, 1981, 95, 180164z.

T. Hayashita et al., *Bull. Chem. Soc. Jpn.*, 1990, 63, 576–580.

Y. Liu et al., *Anal. Chem.*, 1989, 61, 520–524.

J.A.G. Neto et al., *Anal. Chim. Acta*, May 10, 1995, 306, 343–349.

CONTINUOUS FLOW ANALYZING METHOD AND APPARATUS

BACKGROUND OF THE INVENTION

The present invention relates to a continuous flow analyzing method and apparatus, and more particularly to an analyzing method and apparatus for performing an automatic measurement with high precision over a wide quantitative measurement range. More particularly, the invention relates to a continuous analyzing method and apparatus using a flow injection method.

According to a flow injection analyzing method, a continuous flow of controlled carrier is prepared by using a constant flow rate pump, a sample is injected into the flow and reacted with a color reagent or the like, if necessary, and the continuous flow containing the sample is introduced into a detector to thereby carry out quantitative measurement of the target components. Since the reaction with the reagent, the introduction into the detector, the discharge and the like are automatically carried out after the injection of the reagent, the flow injection analyzing method has the advantage that a large amount of samples can be automatically and quickly measured and is used in a wide range of applications including analyses from clinical research and use in determining public pollution.

However, in the above-described method, the quantitative measurement itself is carried out by a detector interposed in the flow path and the detection precision depends, therefore, upon the detection method (in general, absorptiometry, fluorophotometry, atomic absorption spectrometry, flame photometry, ICP emission spectrophotometrical analysis, ICP mass spectrometric analysis) and the characteristics of the detector used in the method. Accordingly, it is necessary to control the sample solution and the arrangement and structure of the analyzing system such that quantitative analysis by the detector is most precisely carried out.

More specifically, in the case where it is expected in advance that the target component in the sample has a high or low concentration, it is necessary to dilute or condense the sample solution in a batch manner or to change the reaction path (reaction coil length or the like) or to control the detection sensitivity of the detector or the injection amount of the sample. Among these approaches, with the batch manner concentration adjustment or the change or adjustment of the arrangement of the apparatus, a long time and a large amount of work are required. Thus, the advantage of the automatic system can not be enjoyed. Accordingly, it is desirable to provide a practical method for controlling the sample injection amount and the measurement concentration.

In a measurement system of a general flow injection method, a measurement container (sample loop) filled with sample for a predetermined capacity is juxtaposed with the carrier flow path for switching the carrier flow to the sample loop side, and the entire amount of the sample filled in the sample loop is extruded for introduction with the carrier flow into a measurement system. It is therefore possible to change the sample injection amount by changing the capacity of the sample loop. The change of the capacity of the sample loop can be carried out by changing the length of tubes used therein for each sample. More specifically, the tubes are exchanged for every sample, or otherwise a syringe-like variable capacity portion is provided in a part of the sample loop (see Japanese Patent Application Laid-Open No. Sho 59-3359 or Japanese Examined Patent Publication No. Hei 2-15031). However, the former method is troublesome and is not suitable for the purpose of processing a large amount of sample in a short period of time. Also, the latter method suffers from a disadvantage that a sample having a high salt concentration tends to clog the path since the structure of the sample injection portion is complicated. Also, it is difficult to automatically control the injection amount.

A method is also known in which the injection amount is adjusted by injecting the sample from the outside of the flow path into the carrier flow path for a predetermined period of time. J. L. Burugera et al. (Anal. Chem. Acta., 234, 253, 1990) and M. L. Guardia et al. (Fresenius' Z. Anal. Chem., 345, 579, 1993) disclose an apparatus using a variable volume injector in which sample measurement holes having different volumes are provided in a rotor for that purpose. Also, Japanese Patent Application Laid-Open No. Hei 5-302871 discloses an apparatus provided with a flow path switching valve. However, in the former apparatus, the sample can be injected only by a predetermined standard volume. In any case, it is difficult to exactly inject the amount of the sample needed for the measurement.

It has also been proposed to use a method in which a sample is first injected into a diluent flow, and only the portion corresponding to a predetermined range of the concentration gradient is introduced into the carrier flow by utilizing the concentration gradient of the sample formed in the diluent flow (Japanese Patent Application Laid-Open No. Hei 4-77662). However, the dispersion of the sample in the diluent flow is not always simple. According to such a method, it is difficult to determine which part of the diluent flow is picked up. In order to calculate the concentration of the original sample from the obtained measurement values, it is necessary to consider a number of factors such as viscosity of the sample, flow resistance of the flow system and the like. A large measurement error is inevitable.

Also, in any method, since the sample injection amount is set in advance corresponding to a range of the concentration which is usually expected from the origin of the sample, even in the case where a large amount of the sample is quickly processed, it is necessary to set the sample loop length or the variable capacity in conformity with each sample, which is troublesome. Furthermore, since there is an inevitable physical limit in setting the sample loop length or the variable capacity, the switching of the sample injection amount has to be carried out in a batch manner. It is impossible to effect continuous measurement. In view of this fact, if the injection amount can be changed as desired without exchanging sample loops, it will be quite convenient.

SUMMARY OF THE INVENTION

In order to overcome the various problems inherent in the conventional flow injection analyzing method, an object of the present invention is to provide a continuous flow analyzing method and apparatus in which the quantitative analysis range is wide and a high precision measurement can readily and quickly be attained.

The present inventors previously developed a fine amount Cd automatic analyzing method by improving the flow injection analyzing method and filed Japanese Patent Application No. Hei 5-289206 entitled "Method for measuring concentration of cadmium in refined liquid for zinc electrolysis". The disclosure of the measurement method and apparatus in Japanese Patent Application No. Hei 5-289206 is hereby incorporated by reference. According to the present invention, this prior method is further improved in view of the above-described standpoints, and it is possible not only to automatically measure the amount over a wide concentration range but also to automatically measure a cadmium concentration of 0.005 ppm or less which could not be automatically analyzed according to the conventional technology.

The present inventors reviewed the method of controlling the sample injection quantity in a continuous flow analyzing method such as a flow injection method. As a result, the present inventors have found that the following modification is useful. In the above-described sample loop method, the opening/closing period of time of the container for holding the sample or the like is adjusted or controlled so that the sample contained in the container is extruded (or introduced) into the carrier separately several times; all of the amount of the sample is not injected at once. Subsequently, the injection amount of the sample is increased/decreased in response to the detection sensitivity so that the detection sensitivity is adjusted to an optimum sensitivity region of the detector for the specific quantitative analysis. This technique utilizes the advantage of the continuous measurement for a high precision result.

In order to overcome the above-described defects there is provided, according to the present invention, a continuous flow analyzing method wherein a sample is injected into a continuously flowing carrier and the sample is introduced into a detector by the carrier to thereby perform a quantitative analysis contained in the sample, comprising the following steps of: filling the sample to be analyzed in a sample introduction switchover valve (SISV); first injecting a portion of the sample from the SISV to the carrier and conducting an analysis thereof; continuously analyzing the sample by, in the case where a detection peak obtained in the detector is below an optimum analysis range, increasing an injection amount of the sample, and in the case where the detection peak obtained in the detector is above the optimum analysis range, decreasing the injection amount of the sample; and repeating the adjustment of the detection peak so that the detection peak reaches the optimum analysis range.

The continuous flow analyzing method comprises the steps of: in the case where a sample filling portion of the SISV is opened/closed so that the sample in the SISV is introduced into the flow of the carrier by means of carrier introduced into the sample filling portion, increasing/decreasing the injection amount of the sample by increasing/decreasing the opening/closing time of said sample filling portion and/or a flow rate of the carrier; and adjusting the detection peak within the optimum analysis range to thereby conduct the quantitative analysis.

The continuous flow analyzing method may further comprise a step for concentrating a component to be measured, provided in the process between the sample injection and the detection, so that the quantitative analysis is conducted after increasing the concentration in the concentrating process.

The concentrating process includes adsorbing the component to be measured in an adsorbing portion provided between an output of the SISV and the detector and eluting the component to be measured from the adsorption portion, the component being eluted and introduced to the detector after concentrating the component to be measured by repeating said adsorbing step.

According to another aspect of the invention, there is provided a continuous flow analyzing apparatus wherein a sample is injected in a continuously flowing carrier and the sample is introduced into a detector by the carrier to thereby perform a quantitative analysis, comprising: a detector; a flow path for introducing, into the detector, the continuous flow of carrier formed by a liquid feed pump; and an SISV interposed in said flow path, wherein said SISV has a sample filling portion for holding the sample to be analyzed and a switchover valve for opening/closing the sample filling portion relative to the continuous flow; said SISV and detector being connected to each other by a control means for automatically controlling an opening/closing time of the switchover valve in response to a detection peak that is obtained by the detector, whereby a feedback function is provided such that an injection amount of the sample is increased/decreased in response to the detection peak obtained by the detector.

According to the invention, there is provided, interposed in the flow path from said SISV to said detector, means for concentrating the component to be analyzed, which is contained in the sample.

The concentrating means comprises an ion-exchange column.

The continuous flow analyzing apparatus can comprise: a pretreatment column for changing a non-ionic component contained in the sample into a soluble component having an ionic property before injecting the sample into the continuous flow carrier.

The sample can be a waste water containing a fine amount of cadmium, and said pretreatment column can be a pretreatment reaction column for reacting the sample to be analyzed with sulfuric acid or nitric acid.

DESCRIPTION OF THE PREFERRED EMBODIMENTS

The present invention can be applied to a general continuous flow analyzing method and in particular is useful in conjunction with a flow injection method. Accordingly, in the following description, the flow injection method will be mainly explained. However, the present invention is applicable to any other continuous flow analyzing method such as liquid chromatography, gas chromatography or the like.

Figure 1:
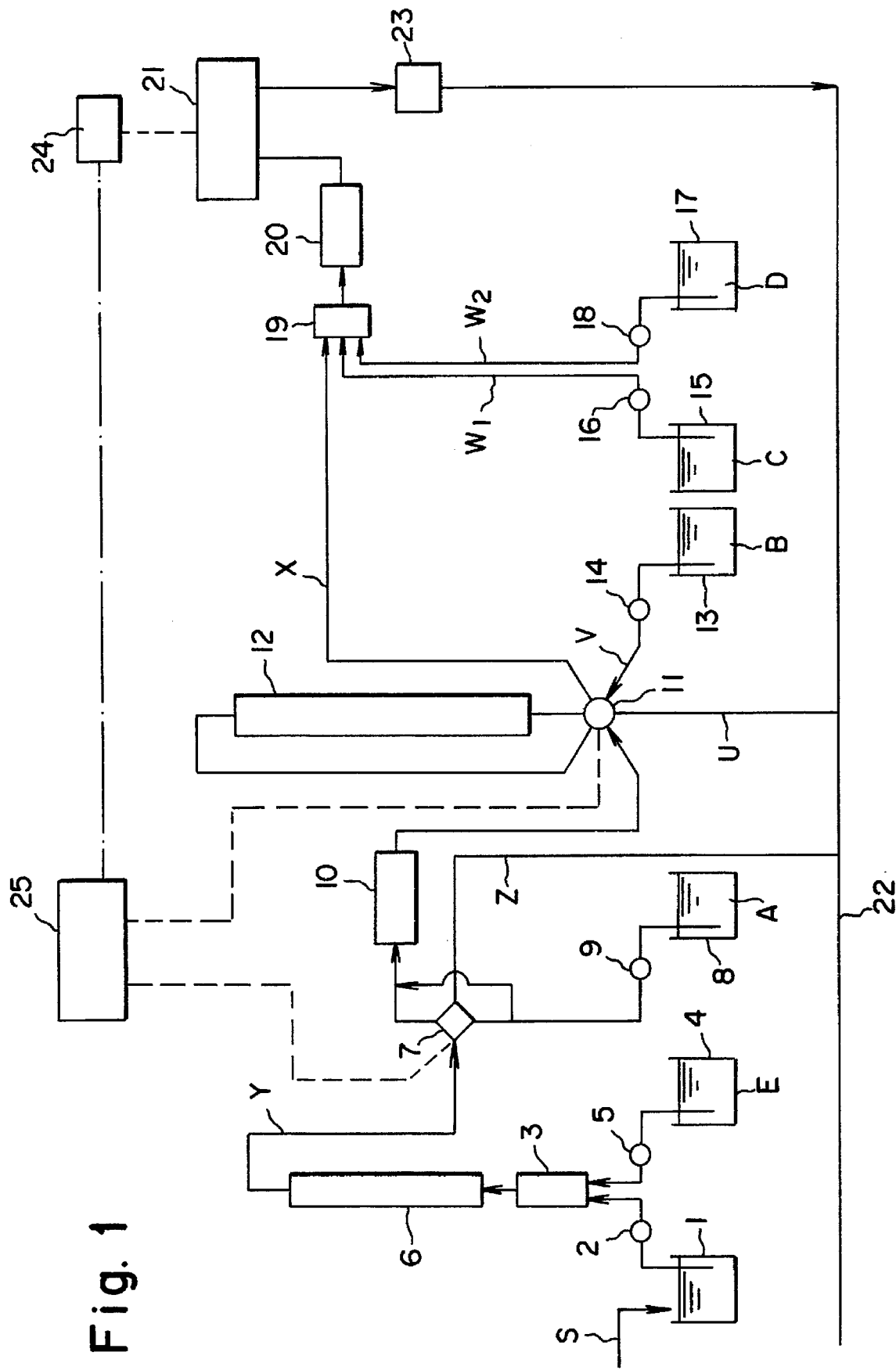
FIG. 1 is a schematic view showing a measurement system according to the present invention.

FIG. 1 schematically shows one example of a flow injection analyzing apparatus according to the invention.

The apparatus shown in FIG. 1 is substantially the same as that described in Japanese Patent Application No. Hei 5-289206 but the difference therebetween is that in the present invention, a pretreatment column is provided because a waste water containing a low concentration of Cd or the like is measured, and in addition a feedback function is applied to the apparatus for increasing/decreasing the injection amount of the sample in response to a detected peak.

As shown in FIG. 1, the flow injection analyzing apparatus according to the present invention has a carrier supply source 8, a quantitative analysis detector 21 and a flow path X extending from the supply source 8 to the detector 21. A liquid feeding pump 9 for pumping the carrier to the flow path X and an SISV 7 for introducing the sample into the flow path X are interposed in the flow path X. A reaction portion 20 for accelerating a color reaction or the like is provided between the SISV 7 and the detector 21. Ordinary tubes can be used as the flow paths. For example, the tubes can be resin tubes made of fluororesin or the like or metal tubes made of stainless steel. A plunger type pump or the like having a small pulsating flow is preferably used as the liquid feeding pump 9. A coil-shaped tube is used as the reaction portion 20, but it is possible to optionally use a temperature controller for accelerating the reaction. Incidentally, although not shown in FIG. 1, necessary flow paths, devices and the like are provided in the carrier flow path X as is well known in the art. For example, paths, valves, flowmeters, and a drain pan for introducing reactive reagent are provided and a back pressure control means 23 is provided as desired.

Figure 2A:
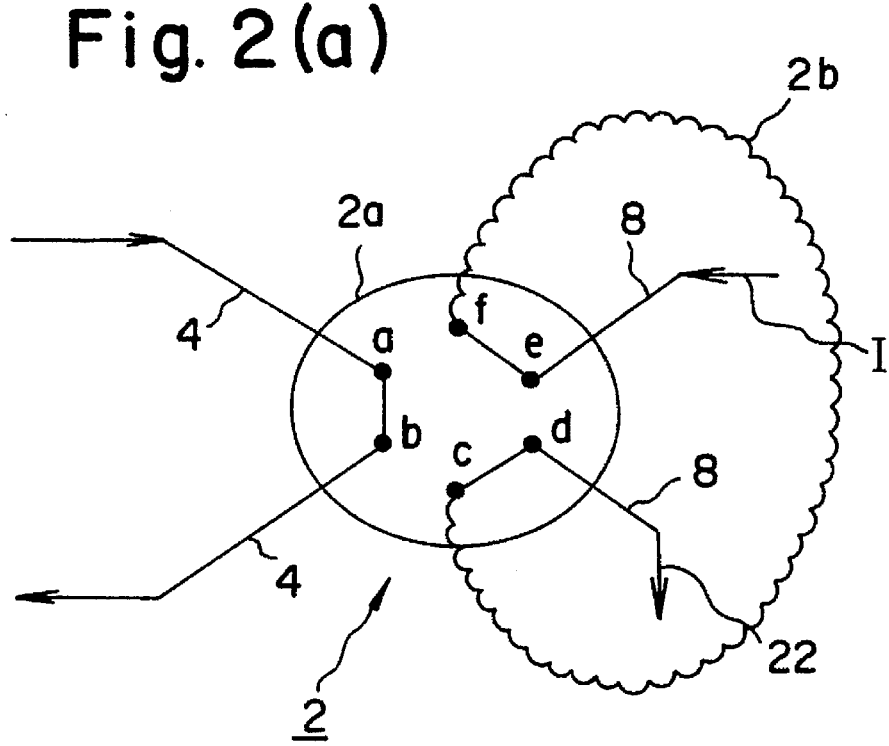
FIGS. 2(a) and 2(b) are schematic views showing sample containers, FIG. 2(a) showing an open state and FIG. 2(b) showing a closed state.
Figure 2B:
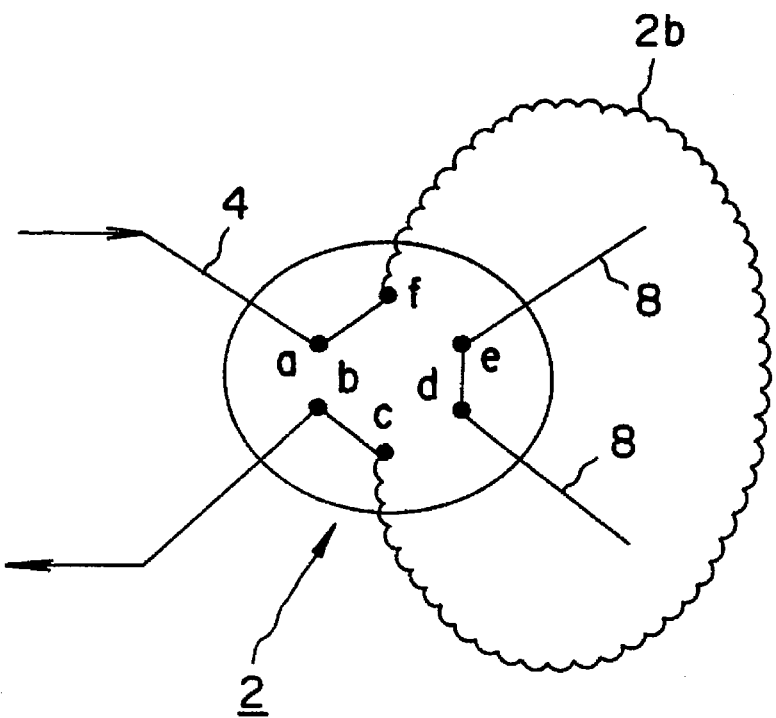

SISV 7 has a sample filling portion for holding the sample and functions as a switchover valve for opening/closing the sample filling portion relative to the carrier flow. FIGS. 2(a) and 2(b) schematically show a preferred example of SISV 7 which is a six-way valve. As shown in FIGS. 2(a) and 2(b), the SISV 7 is composed of a valve body 2a having six through-holes a to f arranged at equal intervals along the circumference and a holding tube 2b integrally provided with the valve body 2a. The valve body 2a can optionally rotate. The holding tube 2b is a portion for receiving and holding the sample and is connected to a through-hole c at one end and to a through-hole f at the other end. Also, the through-holes a and b are in communication with the carrier flow path X and the through-holes d and e are in communication with the sample solution supply source 1 through a flow path Y. When the sample filling portion (holding tube 2b) is closed against the flow path X, the through-holes a and b are in communication with each other through an interior flow path within the valve body and the through-holes c and d, and e and f are in communication with each other, respectively. The carrier flows to the flow path X through the through-holes a and b. On the other hand, the sample solution is filled in the holding tube 2b from the supply source 1 through the flow path Y and the through-holes c, d, e and f. In the case where the sample is injected into the flow path X, the flow paths within the valve body are switched by rotating the valve body 2a, and the flow path from the through-hole c to the through-hole d and the flow path from the through-hole e to the through-hole f are interrupted, whereas the flow path from the through-hole a to the through-hole f and the flow path from the through-hole b to the through-hole c are opened, so that the carrier is introduced to the holding tube 2b through the through-holes a and f and the sample filled in the tube is extruded by the carrier and is fed to the flow path X through through-holes c and b. Since SISV 7 has the above-described structure, it can control the feed-out amount of the sample in accordance with the opening/closing time of the valve body 2a. Incidentally, in the case where the SISV 7 is returned back to the closed position after the injection of the sample, in order to discharge the carrier residing in the holding tube 2b, the flow path Y is branched to the flow path Z through SISV 7, the flow path Y is communicated with a drain path 22 by SISV 7, the carrier is extruded from the drain path by the sample liquid introduced from the supply source 1, and thereafter, SISV 7 is switched over to the sample liquid side to thereby fill the holding tube 2(b) with the sample liquid. SISV 7 may be used equally irrespective of the numbers of the through holes and the inner flow paths if these components have the same functions as those described above.

The detector 21 and SISV 7 are connected to each other by a valve switchover control unit 25 (hereinafter referred to as VC) for controlling the opening/closing time of SISV 7 in response to the measured detection sensitivity. VC 25 is controlled by a signal of an arithmetic unit 24 such as a computer or a comparator. The opening/closing of SISV 7 can be carried out by, for example, driving a relay in accordance with a signal derived from VC 25 and driving a stepping motor in a well known manner.

The analyzing method according to the present invention is carried out as follows.

First of all, the liquid feeding pump 9 is driven under the condition that the SISV 7 is closed. Under this condition, the carrier flow path X and the sample holding tube 2b are separated from each other and the carrier is fed from the carrier supply source 8 to the flow path X by the pump 9. A continuous flow which is from the through-hole a to the through-hole b via the inner flow path of a to b of the valve body and exits at the flow path X to reach the detector 21 via the reaction portion 20 is formed. On the other hand, the holding tube 2b is filled with the sample from the sample supply source 1 through the flow path Y.

When the continuous flow within the carrier flow path is stabilized, SISV 7 is switched over to the open position under the control of VC 25 for a predetermined period of time. In this position, since the carrier is introduced from the through-hole a through the through-hole f to the holding tube 2b, the sample is caused to extrude from the through-hole b to the carrier flow path by the carrier. After a predetermined time, SISV 7 is returned to the closed position, and the sample that has been extruded into the flow path X is fed to the reaction portion 20 by the carrier flow. The sample is reacted with the color reagent or the like contained in the carrier or introduced midway in the flow path and thereafter is introduced into the detector 21.

The detector 21 measures the concentration of the target component contained in the sample. If the detection concentration is excessive, as shown by curve a in FIG. 3, a peak profile that remarkably exceeds an upper limit of an optimum analysis region is exhibited. In this case, since the peak a of the detection concentration exceeds the optimum analysis region, it is impossible to carry out an exact concentration measurement. In case of such a peak level, the opening time of SISV 7 is shortened by VC 25 to reduce the sample injection amount to be fed to the flow path X and the measurement of the concentration is again carried out. The adjustment of the opening/closing time of SISV 7 can be carried out either in a constant quantity way or in a constant rate way. This may be based upon a control value that has been calculated by the arithmetic unit 24 in response to a displacement from the optimum analysis region. Otherwise, an image display unit or the like for displaying the detection concentration is provided and an operator can designate a decreasing amount or rate on the basis of the display.

As a result of the reduction of the opening/closing time of SISV 7, a smaller amount of the sample than the previous injection amount is introduced into the carrier flow path from SISV 7 and the concentration measurement is again carried out. The measured peak level is compared with the optimum analysis region in the same manner as described above. Thereafter, similar steps are repeated until the peak level reaches the optimum analysis region and finally, as shown by curve b in FIG. 3, the peak profile of the measurement concentration is controlled to a position which is somewhat lower than the upper limit of the optimum analysis region to thereby carry out the concentration measurement. As a result, it is possible to perform the quantitative measurement with high precision.

Figure 3:
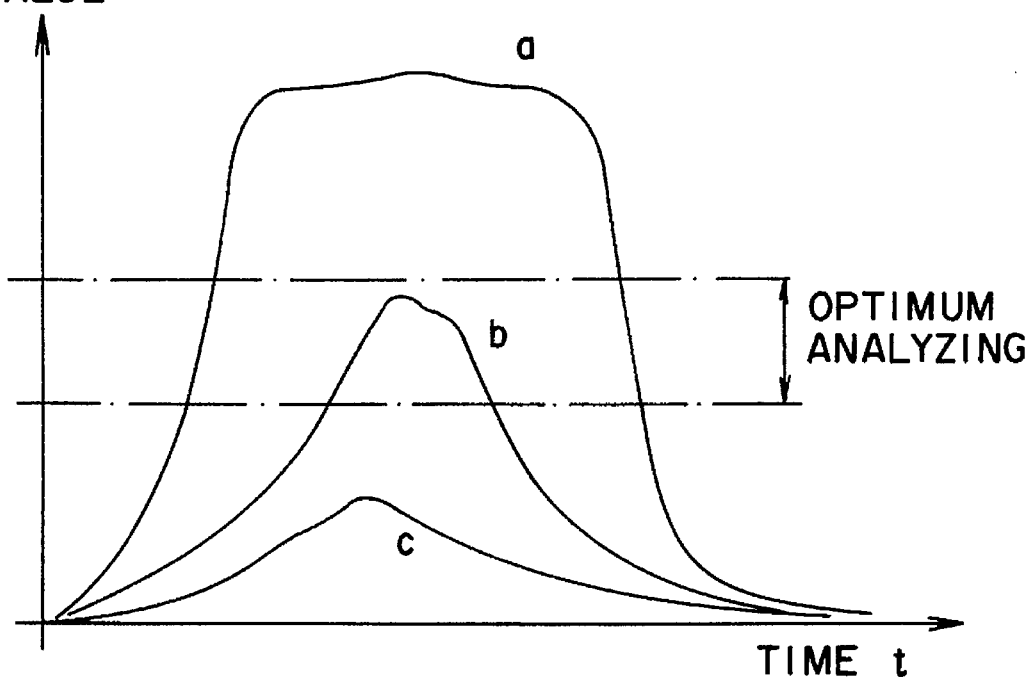
FIG. 3 is a graph showing a concentration peak profile of the analysis results.

On the other hand, in the case where the concentration is too low, as shown by curve c in FIG. 3, the peak profile of the detection concentration is remarkably below the optimum analysis region. In this case, the characteristics of the apparatus are not well utilized and the precision is low. In case of such a peak level, the opening time of the SISV 7 is increased by the VC 25 to thereby increase the injection amount of the sample. Then, the measurement is carried out. Similar steps are repeated until the peak level reaches the optimum analysis region and finally, as shown by curve b in FIG. 3, the peak profile of the measurement concentration is controlled to a position which is somewhat lower than the upper limit of the optimum analysis region to thereby carry out the concentration measurement. As a result, it is possible to automatically perform the quantitative measurement with high precision.

In addition to the control of the sample injection time, or independently of this control, it is possible to control the liquid feeding pump 9 to increase or decrease the liquid feeding rate. In the description of the present specification, the term "optimum analysis region" means a range where a suitable analysis result can be obtained in the detector 21. Such a range is determined by the characteristics of the detector 21. For example, the status of identification between the optimum peak shape calculated based upon the flow resistance of the flow path and the viscosity of the sample or the like and the obtained peak profile is examined in the arithmetic unit 24 according to a suitable shape analysis method. Otherwise it is possible to judge the result of measurement based on whether or not the peak level is in the optimum analysis region.

As described above, according to the present invention, the opening/closing time of SISV 7 with respect to the carrier flow path X is precisely controlled so that the injection amount of the sample solution to the continuous flow analyzing system is precisely controlled. The injection amount of the sample solution is continuously stepwise increased or decreased to thereby adjust the peak profile of the detection concentration and to make it possible to carry out a high precision quantitative analysis.

In general, the concentration change of the sample injected into the closed flow system follows Taylor's dispersion theory. If this is applied to the flow injection, the sample concentration is given as follows:

$$C_A/C_0 = (ut_i \cdot V)/\pi a^2 L^\circ \frac{1}{2} \delta^{1/2}$$

where $C_A$ is the concentration of the sample within the system, $C_0$ is the initial concentration of the sample, u is the flow rate, $t_i$ is the sample injection time, a is the inner diameter (radius) of the carrier flow path, L is the length of the tube from the sample container 2 to the detection position, V is the sample injection amount, and $\delta$ is the dispersion coefficient. Incidentally, $\delta = D/uL$ where D is the diffusion coefficient.

Accordingly, the parameters of the individual measurement are the flow rate u of the carrier and the sample injection time $t_i$, and it is possible to accurately calculate the initial sample concentration $C_0$ from these values and the value (measured value) of $C_A$.

In case of an extremely low concentration, a concentrating portion is provided upstream of the detector 21. The concentrating portion is provided with a concentrating unit 12 and a switchover valve 11. A suitable example of the concentration unit 12 is an adsorption column filled with ion-exchange resin for adsorbing the measurement target component. A flow path V for introducing eluent for separating and eluting the measurement target component from the adsorption material is connected to the switchover valve 11.

The analysis steps in case of the provision of a concentrating portion are as follows.

The sample introduced into the carrier by the opening/closing of the SISV 7 flows through the carrier flow path and enters the concentrating unit (adsorption column) 12 where only the measurement target component is selectively adsorbed. After the adsorption is repeated several times, the eluent is introduced in to the adsorption column 12 by the switchover operation of the switchover valve 11. After eluting, the carrier again is introduced into the adsorbing column 12 by the switchover operation of the switchover valve, and the eluate is introduced into the detector 21 together with the carrier and the concentration measurement is performed. In the case where the detection result is under the optimum analysis region as indicated by the curve c in FIG. 3, the opening/closing time or the number of the opening/closing operations of the SISV 7 are adjustably increased to increase the concentration of the adsorption column 12 so that the peak level reaches the optimum analysis region and the peak profile is obtained in the optimum analysis region to thereby perform a high precision quantitative measurement.

Incidentally, in the case where there is no suitable material that adsorbs the measurement target component, as explained in conjunction with Example 1 to be described below, the measurement target component is transformed into a suitable shape of a complex ion or the like prior to the concentration. Also, an adsorption column can be provided for the purpose of not only concentrating the low concentration component but also separating the measurement target component contained in the sample liquid away from the other components.

EXAMPLE 1

The quantitative analysis of cadmium contained in a zinc sulfate solution for zinc electrolysis was carried out using the analyzing apparatus according to the present invention as schematically shown in FIG. 1. The concentrating portion 12 was provided with an adsorption column filled with ion-exchange resin (tradename: Bio Rad AG1-X8, Cl⁻ type) for concentrating cadmium, a valve 11 for introducing eluent (B liquid), supply portions 15 and 17 for two kinds of detection reagents, i.e., C liquid and D liquid, and a mixer 19 for introducing the reagents to the carrier flow path X. The flow path V through which the eluent will flow was in communication with the ion-exchange adsorption column 12 through the valve 11. A discharge path U was branched from the valve 11. Flow paths $W_1$ and $W_2$ through which the reagents (C and D liquids) would flow were connected to the flow path X through the mixer 19. A reaction coil 20 was interposed between this mixer and the detector 21.

An aqueous solution of 0.1M potassium iodide was used as the carrier (A liquid), and 1M nitric acid solution was used as the eluent (B liquid). With respect to the components of the C liquid and the D liquid, mixed liquid (sodium citrate of 5 g/l, sodium-potassium tartrate of 2.5 g/l, sodium chloride of 3 g/l, potassium hydroxide of 2M) was used as the C liquid, and mixed liquid (Cadion of 0.006% (w/v), potassium hydroxide of 0.1M and Triton-X100 of 0.1% (w/v)) was used as the D liquid. The flow path X was constituted by a Teflon tube having an inner diameter of 1 mm and a connector made of Teflon. Also, SISV 7 for introduction of the sample was an ordinary sample loop (a Teflon tube having an inner diameter of 1 mm, a length of 15 cm, and an inside capacity of 350 µl). An absorptiometer (measurement wavelength: 480 nm) on which a flow cell was loaded was used as the detector 21. A six-way valve was used as SISV 7. The liquid feeding pump and the absorptiometer were controlled by a computer 24. Incidentally, the analysis precision was such that the upper limit of a linear region of a measurement line at which the Cadion of 0.006% might be measured, was set as the upper limit value in terms of the absorptiometric level, and the region within 90% thereof was used as the optimum analysis region. In case of a measurement concentration excess, an injection amount of the sample was decreased by 50% relative to an initial injection amount of the sample and the injection amount was further decreased in a stepwise manner as by 33% reduction and 66% reduction. Even if the level would not reach the optimum analysis region, the injection amount was reduced substantially in accordance with the above-described reduction rate.

First of all, the sample liquid containing Cd was filled in the holding tube (sample loop) of SISV 7, and the A liquid was caused to flow from the carrier supply source 8 to the carrier flow path X to form the continuous flow. Subsequently, the SISV 7 was opened to introduce the carrier flow into the sample loop and to introduce the sample liquid into the carrier flow. When the sample liquid was introduced into the carrier, the mixed liquid was reacted in the mixer 10 to form an anion complex of iodide ($CdI_4^{2-}$). The anion complex was adsorbed to the adsorption column 12. On the other hand, the valve 7 was switched to the liquid discharge path U in advance, so that a discharge solution was discharged through the flow path U from the adsorption column 12. After the adsorption, the valve 11 was switched to the flow path X, the valve 11 was opened to introduce the eluent B to the adsorption column 12, and after eluting the anion complex of iodide, the valve 11 was closed to introduce the carrier to the adsorption column 12 and to feed out the complex to the flow path X. As a result, the anion complex was mixed with the C liquid and the D liquid introduced into the mixer 19 and was thereafter introduced into the reaction coil 20. The anion complex contained in the liquid was sufficiently mixed with the C liquid and D liquid and became a complex Cd-Cadion having an extremely long absorptive wavelength of 480 nm and was finally discharged from the discharge line 22 after the measurement of absorbance in the detector 21.

In the quantitative measurement, an absorbance of a standard solution whose concentration was known was measured to form the detection line, and the Cd concentration within the sample liquid contained in the sample loop was calculated from the absorbance obtained by the measurement of the sample solution by utilizing the detection line.

Figure 4:
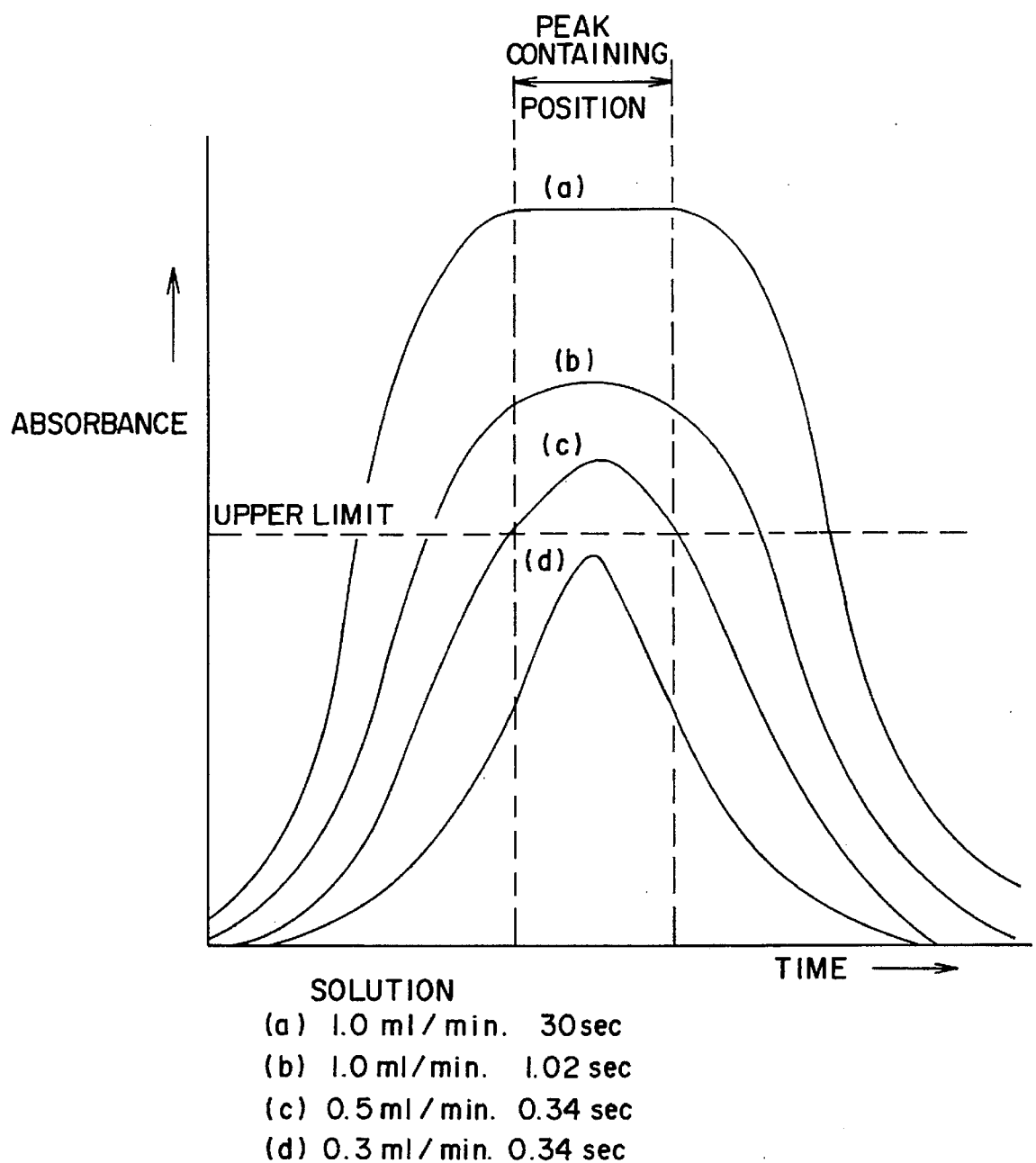
FIG. 4 is a graph showing a concentration measurement result of Example 1.

Under the conditions of an initial carrier flow rate ($V_0$) of 1.0 ml/min and an initial injection time ($t_0$) of 1.02 seconds for the sample, the analysis was started. When the automatic analysis was carried out in accordance with the above-described program, a result was obtained in which the peak level entered the optimum analysis region within five cycles of the analyzing operation (carrier flow rate: 0.3 ml/min and sample injection time: 0.34 seconds). The first, fourth and fifth peak profiles in this analysis are shown by curves b to d in FIG. 4.

EXAMPLE 2

An apparatus similar to that of Example 1 was used and the quantitative analysis of Cd contained in a sample of a zinc sulfate solution for zinc electrolysis having a low Cd content was carried out.

Figure 5:
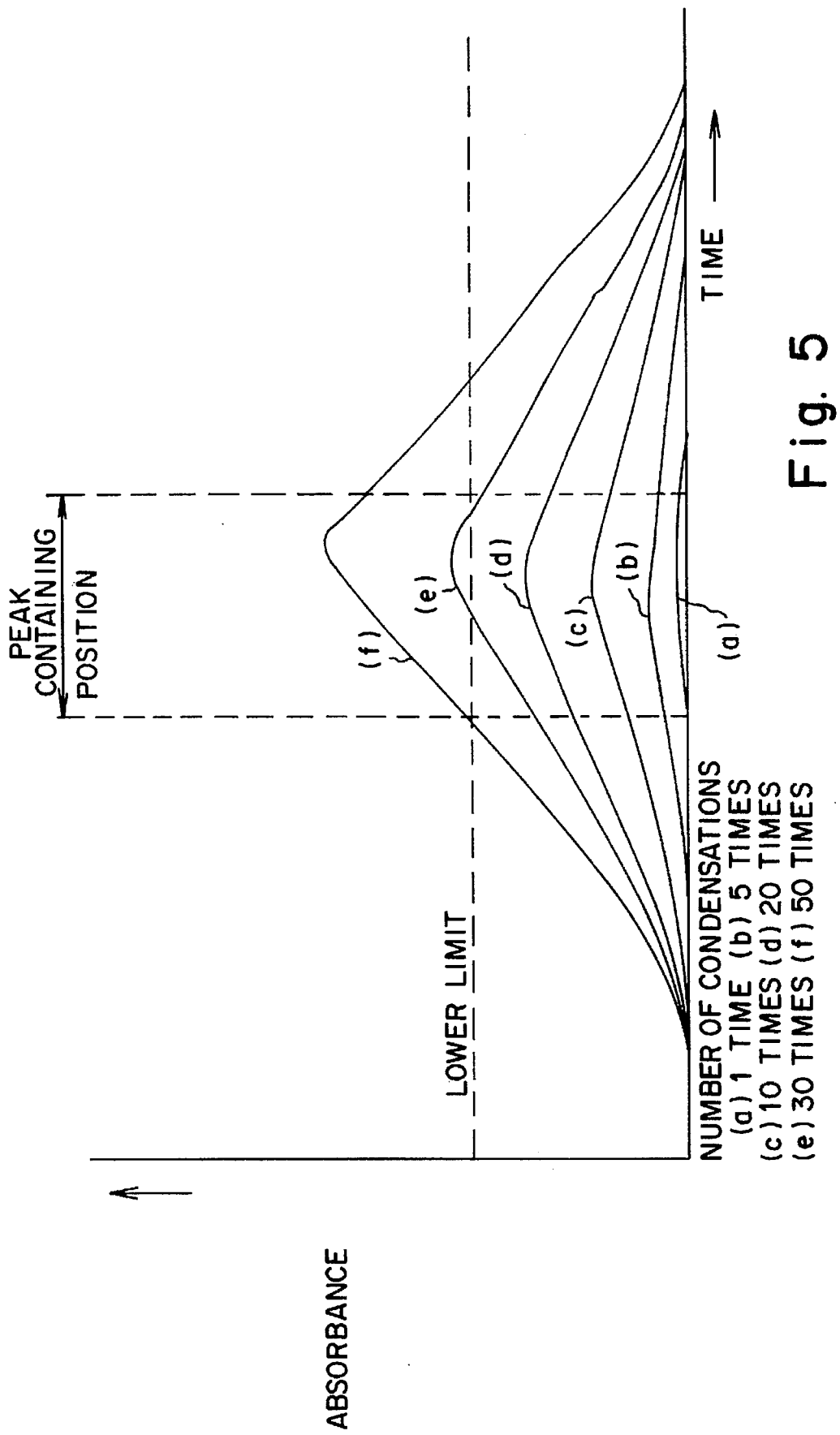
FIG. 5 is a graph showing a concentration measurement result of Example 2.

The analysis steps were similar to those of Example 1 but the number of the sample injections was increased and the amount of $CdI_4^{-2}$ ion adsorbed to the column was concentrated. As shown in FIG. 5, the tip end portion of the peak exceeded the lower set limit of the peak with thirty concentrations. In addition, the measurement result was obtained with a sufficient precision with fifty concentrations.

EXAMPLE 3, Comparison 1

A quantitative analysis of Cd contained in samples of a zinc sulfate solution for zinc electrolysis having a high Cd content was carried out in the same manner as in Example 1. Also, as a comparison, each sample was first injected into a flow of a diluent and, using a concentration gradient of the sample formed in the diluent flow, a measurement was carried out in accordance with a method (Japanese Patent Application Laid-Open No. Hei 4-77662) for introducing only a portion in a specific range of the concentration gradient into the carrier flow. Furthermore, in order to evaluate the measurement precision, the quantitative analysis was carried out through the ICP method. The result is shown in Table 1.

TABLE 1

| | (Measurement Result) | | | | |
|---|---|---|---|---|---|
| | Method of the Invention | | Conventional Method | | ICP |
| Sample Nos. | Analysis Value (ppm) | Measurement Precision (%) | Analysis Value (ppm) | Measurement Precision (%) | Method Analysis Value (ppm) |
| 1 | 950 | 1.2 | 940 | 5.5 | 950 |
| 2 | 800 | 0.6 | 820 | 5.2 | 790 |
| 3 | 830 | 1.1 | 800 | 5.8 | 820 |
| 4 | 740 | 0.8 | 780 | 4.0 | 750 |
| 5 | 300 | 1.3 | 260 | 3.2 | 290 |
| 6 | 260 | 1.0 | 270 | 3.6 | 260 |
| 7 | 50 | 0.9 | 50 | 2.1 | 50 |
| 8 | 44 | 2.5 | 47 | 2.5 | 45 |
| 9 | 29 | 2.0 | 25 | 5.0 | 27 |
| 10 | 5 | 1.5 | 5 | 17.0 | 4 |
| 11 | 6 | 1.7 | 5 | 20.5 | 5 |
| 12 | 1 | 0.3 | <5 | — | 1 |
| 13 | 0.4 | 0.9 | <5 | — | 0.5 |
| 14 | 0.1 | 2.0 | <5 | — | 0.1 |

Note:
the conventional method was based upon Japanese Patent Application Laid-Open No. Hei 4-77662.
Injection time and injection amount of the sample:
Samples 1 to 6: 0.34 seconds, 01. ml/min
Samples 7 to 9: 1.02 seconds, 0.5 ml/min
Samples 10 to 12: 30 seconds, 0.5 ml/min
Samples 13 to 14: 30 seconds, 1.0 ml/min As shown from the results above, it should be understood that according to the present invention it is possible to carry out high precision analyses with respect to samples having a concentration in a wide range in comparison with a conventional method.

EXAMPLE 4, Comparison 2

A quantitative analysis of Cd contained in samples of a zinc sulfate solution for zinc electrolysis having a low Cd content was carried out in the same manner as in Example 2. In order to evaluate the measurement precision, a quantitative analysis using atomic absorption spectrometry (JIS (Japanese Industrial Standard) K0101) was also carried out. The result is shown in Table 2.

TABLE 2

(Measurement Result)

| Sample Nos. | Method of the Invention | | Conventional Method | |
| --- | --- | --- | --- | --- |
| | Analysis Value (ppm) | Measurement Precision (%) | Analysis Value (ppm) | Measurement Precision (%) |
| 1 | 990 | 1.2 | 1,000 | 5.5 |
| 2 | 890 | 0.6 | 900 | 5.2 |
| 3 | 770 | 1.1 | 800 | 5.8 |
| 4 | 640 | 0.8 | 780 | 4.0 |
| 5 | 0.7 | 1.3 | 0.7 | 3.2 |
| 6 | 0.7 | 3.0 | 0.7 | 3.6 |

Note:
Samples 1 to 4: zinc sulfate solution for zinc electrolysis
Samples 5 to 6: waste water
Injection number: samples 1 to 4 (once) and samples 5 and 6 (fifty concentrations)

As shown from these results, according to the present invention, it was confirmed that the analysis precision and the detection sensitivity in the super fine amount analysis could be obtained by effecting the feedback of the data.

Reference Examples

Figure 6:
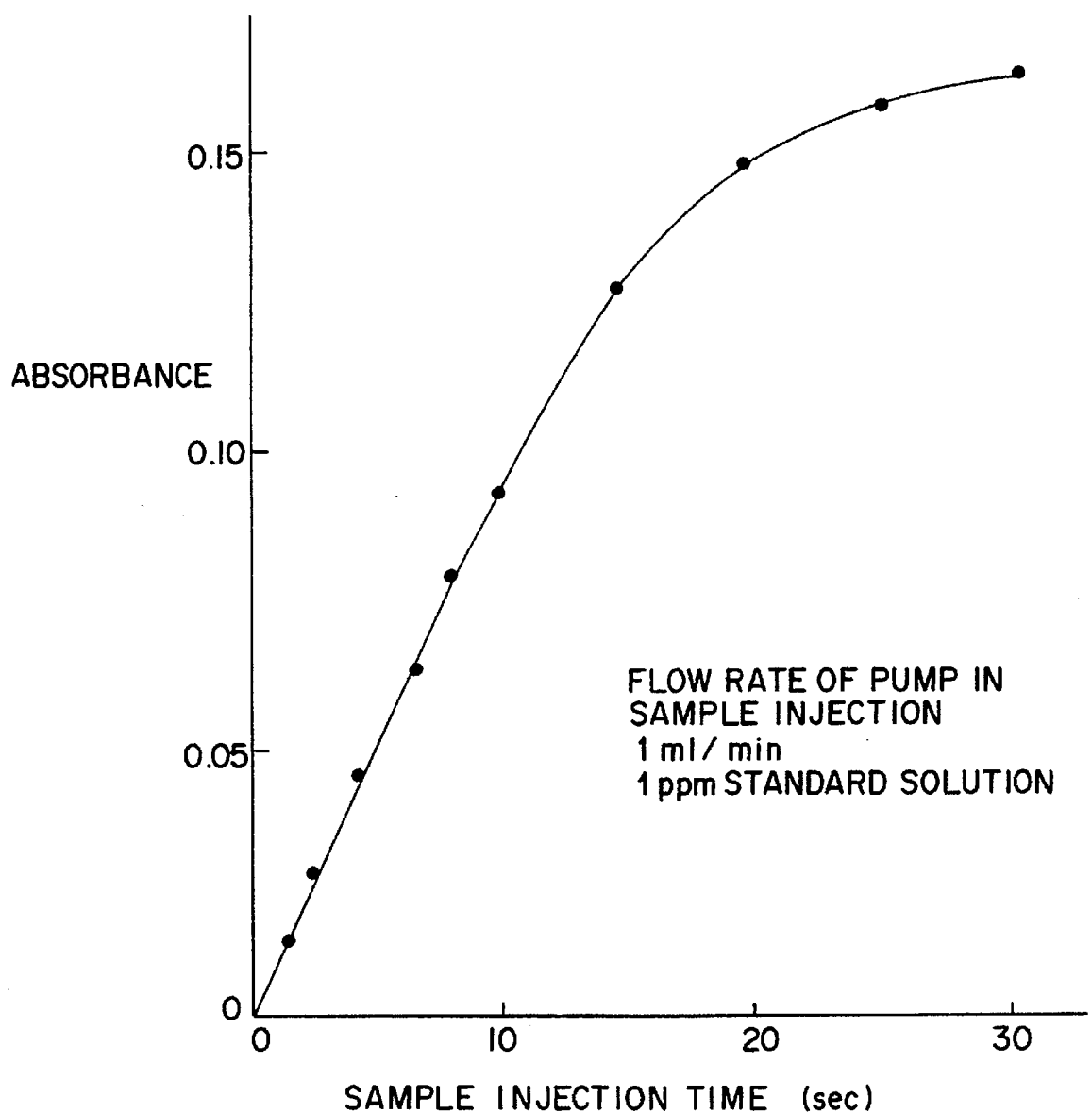
FIG. 6 is a graph showing a relationship between a sample injection time and absorbance in a reference example.
Figure 7:
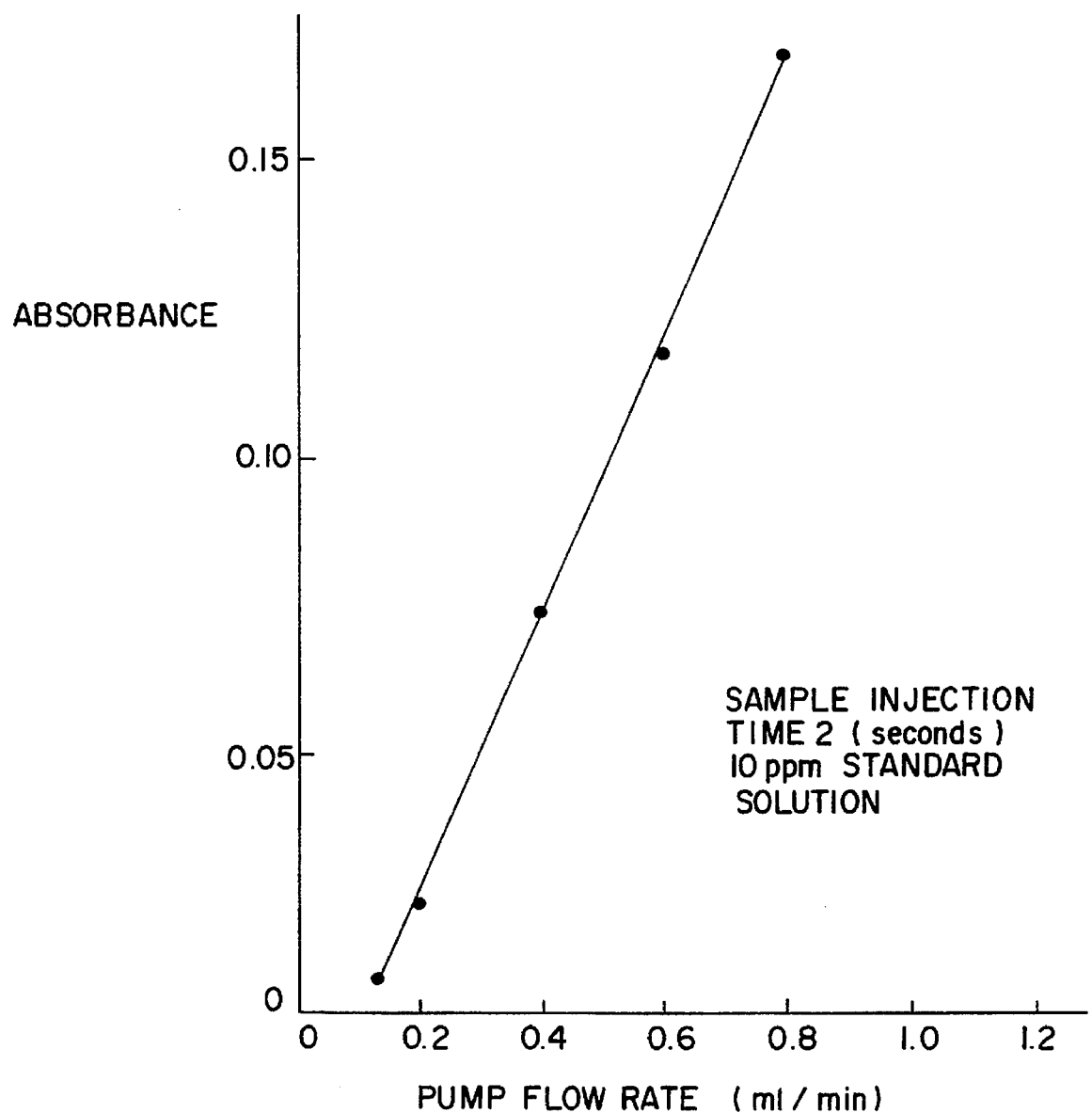
FIG. 7 is a graph showing a relationship between an injection amount and absorbance in a reference example.

The apparatus of the examples was used, and either the sample injection time or the carrier flow rate was changed. Then, the responsiveness of the detector was determined with a Cd standard sample. The results are shown in FIGS. 6 and 7. As is apparent from these drawings, according to the present invention, since the sample injection amount can be accurately controlled by the control of the sample injection time or the carrier flow rate, a linear correlation is established between each parameter and the concentration.

EXAMPLE 5

In this example, Cd content of 0.001 ppm or less contained in the waste water in a cadmium treatment facility was measured.

Since the Cd contained in the waste water was present in the form of a simple substance or in a nonionic form in a state of a precipitate of an oxide, hydroxide, carbonate or in a state entrained in an adsorptive material kept under suspension, in order to introduce it into the automatic analyzing apparatus which utilizes the flow injection method, it was necessary to change the nonionic component of Cd contained in a sample solution of the waste water into a soluble component with an ionic property by subjecting the waste water to a pretreatment. For this reason, the pretreatment reaction column 6 for reaction with the pretreatment reagent (decomposing solution) such as sulfuric acid or nitric acid was provided.

First of all, potassium iodide, sodium iodite, ammonium iodide, potassium hydroxide, sodium citrate, sodium-potassium tartrate, tartaric acid, oxalic acid, sodium oxalate, sodium phosphate, acetylacetone, malonic acid, thiourea, 1,10-phenanthroline, tetraethylene pentamine, concentrated nitric acid, and color reagents 1 to 5 (each being a special grade reagent having a high purity) were prepared. By using the above-described reagents, decomposing liquid (E liquid) having a nitric acid concentration of 0.5 Mol/l, complex forming solution 1 having a potassium iodite concentration of 0.1 Mol/l, complex forming solution 2 having a sodium iodide concentration of 0.1 Mol/l, complex forming solution 3 having an ammonium iodide concentration of 0.1 Mol/l, eluent 1 having a nitric acid concentration of 1 Mol/l, eluent 2 having a sulfuric acid concentration of 1 Mol/l, masking solution, pH adjustment solution, buffer solution, and coloring liquid having a reagent concentration shown in Table 3 were adjusted. The masking agent, the pH adjustment agent and the buffer agent are adjusted as a mixed solution having the concentration shown in Table 3.

TABLE 3

| Kind | Complex Forming Solution | Eluent | pH Adjusting Solution (g/l) | | Masking Solution (g/l) | | Buffer Solution (g/l) | | Coloring Solution (g/l) | | Measurement w.l. *2 (nm) |
| --- | --- | --- | --- | --- | --- | --- | --- | --- | --- | --- | --- |
| | | | Chemical Name | Con. *1 | Chemical Name | Con. *1 | Chemical Name | Con. *1 | Chemical Name | Con. *1 | |
| 1 | Complex Forming Solution 1 | Eluent 1 | potassium hydroxide | 56 | sodium thiosulfate, sodium oxalate | 0.5 2.0 | sodium thiosulfate, sodium oxalate | 0.5 2.0 | coloring agent 2 | 0.01 | 555 |
| 2 | Complex Forming Solution 2 | Eluent 2 | potassium hydroxide | 56 | 1,10-phenanthroline, ammonium oxalate | 0.1 0.5 | ammonium oxalate | 0.5 | coloring agent 3 | 0.03 | 555 |
| 3 | Complex Forming Solution 1 | Eluent 1 | sodium hydroxide | 25 | sodium thiosulfate, sodium citrate | 0.5 2.0 | sodium citrate | 1 | coloring agent 3 | 0.03 | 555 |
| 4 | Complex Forming Solution 2 | Eluent 2 | potassium hydroxide | 56 | 1,10-phenanthroline, malonic acid, sodium dihydrogen phosphate | 0.1 1 0.5 | sodium dihydrogen phosphate | 0.5 | coloring agent 2 | 0.01 | 555 |
| 5 | Complex Forming Solution 1 | Eluent 1 | sodium hydroxide | 25 | 1-10-phenanthroline, sodium oxalate, potassium dihydrogen phosphate, sodium chloride | 0.2 0.5 0.1 5 | potassium dihydrogen phosphate, sodium oxalate | 0.1 0.5 | coloring agent 4 | 0.05 | 600 |

TABLE 3-continued

| Kind | Complex Forming Solution | Eluent | pH Adjusting Solution (g/l) Chemical Name | Con. *1 | Masking Solution (g/l) Chemical Name | Con. *1 | Buffer Solution (g/l) Chemical Name | Con. *1 | Coloring Solution (g/l) Chemical Name | Con. *1 | Measurement w.l. *2 (nm) |
|---|---|---|---|---|---|---|---|---|---|---|---|
| 6 | Complex Forming Solution 2 | Eluent 2 | potassium hydroxide | 112 | thiourea, tetraethylene-pentamine, sodium chloride | 5 1 6 | ammonium chloride | 5 | coloring agent 1, Triton-X100, potassium hydroxide | 0.01 2 5.6 | 480 |
| 7 | Complex Forming Solution I | Eluent 1 | sodium hydroxide | 25 | acetylacetone, malonic acid, potassium tartrate | 0.1 0.1 5 | potassium tartrate | 5 | coloring agent 5 | 0.1 | 500 |
| 8 | Complex Forming Solution 1 | Eluent 1 | potassium hydroxide | 112 | sodium citrate, sodium-potassium tartrate, sodium chloride | 10 5 6 | sodium citrate, sodium-potassium tartrate | 10 5 | coloring agent 1, Triton-X100, potassium hydroxide | 0.02 2 5.6 | 480 |
| 9 | Complex Forming Solution 2 | Eluent 2 | potassium hydroxide | 56 | ammonium dihydrogen phosphate, tetraethylene-pentamine, sodium chloride | 0.5 2 6 | ammonium phosphate | 0.5 | coloring agent 5 | 0.1 | 500 |
| 10 | Complex Forming Solution 3 | Eluent 2 | potassium hydroxide | 56 | ammonia citrate, sodium thiosulfate, thiourea | 3 0.5 5 | ammonium citrate | 3 | coloring agent 4 | 0.05 | 600 |

Note:
*1: concentration
*2: wavelength

Furthermore, in order to confirm the effect of the conventional method, hydrochloride acid, salicylic acid and thiourea which were special grade reagents were prepared. A masking solution containing salicylic acid of 14 mg/l and thiourea of 0.8 mg/l, pH adjusting solution containing NaOH at a concentration of 100 g/l and a buffer solution of acetic acid of 58 g/l were prepared.

Also, a standard solution of cadmium having a concentration of 0.1 g/l prepared by using electrolytic cadmium having a purity of 99.9% or more was diluted to prepare various kinds of a cadmium standard solution having concentrations of 0.001 to 1.1 mg/l. The coloring agents 1–5 and the buffer solution (if necessary) were added to the standard solution to make a coloring reaction. The calibration curves of the various coloring agents were obtained by using a spectrophotometer (Hitachi U-1000 type).

The sample solutions 1–6 including interfering ions (shown in Table 4 below) were sampled from the cadmium treatment facilities 1 to 3.

TABLE 4

| Sample No. | Sample Pick-up Facility | Interfering Ion Concentration (ppm) | | | | | | | | | |
|---|---|---|---|---|---|---|---|---|---|---|---|
| | | Cu | Pb | Fe | Ag | Hg | Bi | Sb | As | Cr | Zn |
| 1 | cadmium facility 1 | 0.3 | 0.09 | 0.8 | 0.020 | 0.001 | 0.05 | 0.1 | 0.30 | 0.4 | 0.9 |
| 2 | cadmium facility 1 | 0.1 | 0.10 | 0.9 | 0.013 | 0.001 | 0.04 | 0.2 | 0.35 | 0.3 | 0.8 |
| 3 | cadmium facility 2 | 0.05 | 0.02 | 0.1 | <0.001 | <0.005 | 0.02 | 0.02 | 0.05 | 0.02 | 0.1 |
| 4 | cadmium facility 2 | 0.07 | 0.02 | 0.1 | <0.001 | <0.005 | 0.01 | 0.01 | 0.08 | 0.05 | 0.2 |
| 5 | cadmium facility 3 | 0.02 | 0.01 | <0.01 | <0.001 | <0.005 | <0.005 | <0.005 | 0.004 | 0.02 | 0.05 |
| 6 | cadmium facility 3 | 0.01 | 0.02 | <0.01 | <0.001 | <0.005 | <0.005 | <0.005 | 0.002 | 0.01 | 0.04 |

The sample solutions 1–6 were introduced into a sample receiving container 1, and were mixed with the above-described decomposing solution while being fed into a pretreatment mixer 3. Thereafter, the mixture was heated at 135° C. in a pretreatment column composed of a tube made of Teflon having a length 15 m so that nonionic cadmium compounds such as colloidal cadmium compounds were converted to have an ionic property. By using a sample loop having 2,000 μl provided in SISV 7, the sampling solution was sampled. The solution was concentrated by using a column made of polyethylene having an inside diameter of 10 mm, filled with a strong basic anion-exchange resin (Dowex-1-X8, 100–200 mesh, Cl type) of 2 g, repeatedly by 30 to 50 times. Thereafter, methods 1 to 10 according to the present invention were conducted under the conditions shown in Table 3. The cadmium concentration in the sample solution shown in Table 5 was measured by using the calibration curve of the above-described spectrophotometer.

In comparison, hydrochloride acid was added to the sample solutions 1 to 6 and adjusted so as to have an acid solution of 1.2 normal. Thereafter, 200 ml of this solution was picked up and was caused to pass through a 15 ml basic anion-exchange resin phase (Dowex-1-X8) of 15 ml (10 g), which had been sufficiently washed with the hydrochloride acid of 1.2 normal. The cadmium ions were adsorbed into the resin and furthermore sufficiently washed with the hydrochloride acid of 1.2 normal. Thereafter, nitric acid solution of 0.1 normal was caused to pass through the above-described ion-exchange resin layer to elute the cadmium. The buffer solution of 5 ml was added to the obtained eluate of 60 ml to maintain a pH of 5 to 6. The masking solution prepared for the above-described conventional method was further added thereto and was sufficiently agitated to give a measurement solution having a constant volume of 100 ml. Thereafter, the cadmium ion concentration of the measurement solution was measured by using an ion meter (made by Toa Denpa Kogyo, 1M-40S) provided with cadmium ion electrodes (made by Toa Denpa Kogyo, CD-125) calibrated in advance by using a cadmium standard solution. The cadmium ion concentrations of the sample solutions 1 to 6 were measured as shown in Table 5.

Furthermore, a cadmium analysis in accordance with an ICP emission spectrochemical analysis with respect to the sample solutions 1 to 6 were conducted on the basis of Industrial Drain Water Test Method JIS K0102.55.4. The analyzed values are shown in Table 5 for the purpose of a comparison between a conventional method and the method according to the present invention.

As is apparent from Table 5, the measurement results according to the method of the present invention very well followed the analyzed results according to Industrial Drain Water Test Method defined by JIS. The results according to the invention exhibited a much better constant quantitative measurement property than the measurement results according to the ion meter using the cadmium ion electrodes which was the conventional method.

TABLE 5

| Kind | Sample | | CD Ion Concentration (ppm) | Cd Concentration According to JIS Method (ppm) |
|---|---|---|---|---|
| Method according to the present invention | 1 | 1 | 0.005 | 0.005 |
| | 2 | 2 | 0.006 | 0.006 |
| | 3 | 3 | 0.006 | 0.006 |
| | 4 | 4 | 0.003 | 0.003 |
| | 5 | 5 | 0.004 | 0.004 |
| | 6 | 6 | 0.002 | 0.002 |
| | 7 | 1 | 0.005 | 0.005 |
| | 8 | 2 | 0.005 | 0.005 |
| | 9 | 3 | 0.006 | 0.006 |
| | 10 | 4 | 0.003 | 0.003 |
| Method according to the conventional method | 1 | 1 | 0.0100 | 0.005 |
| | 2 | 2 | <0.001 | 0.005 |
| | 3 | 3 | 0.020 | 0.006 |
| | 4 | 4 | 0.015 | 0.003 |
| | 5 | 5 | 0.005 | 0.004 |
| | 6 | 6 | 0.030 | 0.002 |

According to the present invention, since it is possible to precisely control the sample injection quantity, it is possible to carry out an accurate quantitative analysis in a continuous flow measurement method. Also, since it is possible to apply the method to samples having a low concentration of about 1 ng/ml or a high concentration of up to about 1,000 μg/m with the same apparatus system by feeding the results obtained in the detector back to the sample feed system, the present invention is very useful for automatically analyzing a number of samples having a wide variation range of concentration.

Also, according to the present invention, since it is possible to automatically measure the cadmium concentration of 0.005 ppm or less in waste water in the cadmium relating facility, if the cadmium concentration of the waste water in the cadmium relating facility is continually measured according to the method of the invention and the drain treatment equipment is operated, it is possible to well control the environment. The industrial contribution thereof is remarkable.

Various details of the invention may be changed without departing from its spirit or its scope. Furthermore, the foregoing description of the embodiments according to the present invention is provided for the purpose of illustration only, and not for the purpose of limiting the invention as defined by the appended claims and its equivalents.

What we claim is:

1. A continuous flow analyzing method wherein a sample is injected in a continuously flowing carrier and the sample is introduced into a detector by the carrier to thereby perform a quantitative analysis of the sample, comprising the steps of:

a) filling a sample introduction switchover means with the sample to be analyzed;

b) introducing a partial amount of the sample from the sample introduction switchover means into the carrier;

c) analyzing said amount of the sample from b) in the detector to determine a detection peak;

d) comparing the detection peak obtained in the detector with a predetermined optimum analysis range;

e) continuously analyzing the sample by repeating steps b), c) and d) until the detection peak reaches the optimum analysis range and, in the case where the detection peak obtained in the detector is under the optimum analysis range, increasing the amount of the sample introduced into the carrier, and in the case where the detection peak obtained in the detector is over the optimum analysis range, decreasing the amount of the sample introduced into the carrier.

2. The continuous flow analyzing method according to claim 1, further comprising the steps of:

in the case where the sample introduction switchover means is opened so that the sample in the sample introduction switchover means is extruded into the flow of the carrier by carrier that is introduced into the sample filling portion, increasing or decreasing the amount of the sample by increasing or decreasing the opening time of said sample filling portion and/or a flow rate of the carrier.

3. The continuous flow analyzing method according to claim 1, further comprising the step of:

providing a step for concentrating a component of the sample to the measured between the sample injection step and the detection step so that the quantitative analysis is conducted after increasing the concentration.

4. The continuous flow analyzing method according to claim 3, wherein said concentrating step includes adsorbing the component to be measured in an adsorbing means provided between the output of the sample introduction switchover means and the detector, and eluting the component to be measured from the adsorption portion, wherein the component to be measured is eluted and introduced to the detector after concentration of the component by repeating said adsorbing step.

5. A continuous flow analyzing apparatus wherein a sample is introduced into a continuously flowing carrier and the sample is introduced into a detector by the carrier to thereby perform a quantitative analysis, comprising:

a detector;

a flow path for introducing into the detector, a continuous flow of the carrier formed by a liquid feed pump; and a sample introduction switchover means interposed in said flow path, wherein said sample introduction switchover means has a sample filling portion for holding a predetermined amount of the sample to be analyzed, and a switchover valve for opening and closing the sample filling portion relative to the continuous flow, and wherein said sample introduction switchover means and said detector are connected to each other by a control means for controlling the opening and closing time of the switchover valve to introduce a partial amount of the sample in the sample filling portion into the flow path in response to a detection peak of the sample that is obtained by said detector, whereby a feed back function is performed such that an amount of the sample introduced into said carrier is increased or decreased in response to the detection peak.

6. The continuous flow analyzing apparatus according to claim 5, further comprising a means for concentrating the component to be analyzed, which is contained in the sample, said means being interposed in the flow path between said sample introduction switchover means and said detector.

7. The continuous flow analyzing apparatus according to claim 6, wherein said concentrating means comprises an ion-exchange column.

8. The continuous flow analyzing apparatus according to claim 5, further comprising:

a pretreatment column for converting a nonionic component containing the sample into a soluble component having an ionic property.

9. The continuous flow analyzing apparatus according to claim 8, wherein said pretreatment column is a pretreatment reaction column for reacting the sample to be analyzed with sulfuric acid or nitric acid.

* * * * *

UNITED STATES PATENT AND TRADEMARK OFFICE
CERTIFICATE OF CORRECTION

PATENT NO. : 5,624,846
DATED : April 29, 1997
INVENTOR(S) : Yutaka HAYASHIBE et al.

It is certified that error appears in the above-indentified patent and that said Letters Patent is hereby corrected as shown below:

On the cover page, column 2, line 2 from the bottom of the abstract: change "ug/m" to --ug/ml--.

Column 13, line 34: change "hydrochloride" to --hydrochloric--.

Column 16, line 62: change "sample to the" to --sample to be--.

Signed and Sealed this

Twenty-fifth Day of November, 1997

Attest:

BRUCE LEHMAN

Attesting Officer

Commissioner of Patents and Trademarks